United States Patent [19]

Marcus

[11] Patent Number: 5,006,706
[45] Date of Patent: Apr. 9, 1991

[54] ANALYTICAL METHOD AND APPARATUS

[75] Inventor: R. Kenneth Marcus, Clemson, S.C.

[73] Assignee: Clemson University, Clemson, S.C.

[21] Appl. No.: 359,157

[22] Filed: May 31, 1989

[51] Int. Cl.$^5$ .................................................. H01J 49/04
[52] U.S. Cl. ..................................... 250/288; 250/281; 250/282; 250/423 R
[58] Field of Search ..................... 250/288, 281, 423 P, 250/423 R; 315/111.21, 111.41

[56] References Cited

U.S. PATENT DOCUMENTS

| | | | |
|---|---|---|---|
| 3,860,507 | 1/1975 | Vossen, Jr. | 204/298 |
| 3,915,764 | 10/1975 | Noreika et al. | 204/192 |
| 3,944,826 | 3/1976 | Gray | 250/288 |
| 4,166,952 | 9/1979 | Colby et al. | 250/288 |
| 4,262,631 | 4/1981 | Kubacki | 204/164 |
| 4,339,691 | 7/1982 | Morimiya et al. | 250/281 |
| 4,355,262 | 10/1982 | Chan et al. | 315/111.41 |
| 4,363,828 | 12/1982 | Brodsky et al. | 427/39 |
| 4,620,102 | 10/1986 | Watanabe et al. | 250/288 |
| 4,692,630 | 9/1987 | Gagol | 250/423 R |
| 4,693,805 | 9/1987 | Quazi | 204/298 |
| 4,715,054 | 12/1987 | Kato et al. | 315/111.21 |
| 4,746,802 | 5/1988 | Kellerhals | 250/288 |
| 4,760,253 | 7/1988 | Hutton | 250/288 |
| 4,760,820 | 8/1988 | Tozzi | 315/111.41 |
| 4,812,040 | 3/1989 | Marcus et al. | 250/288 |
| 4,849,628 | 7/1989 | McLuckey et al. | 250/288 |
| 4,853,539 | 8/1989 | Hall et al. | 250/288 |

FOREIGN PATENT DOCUMENTS 2616545  6/1987  France .

OTHER PUBLICATIONS

Donohue and Harrison, "Radiofrequency Cavity Ion Source in Solids Mass Spectrometry", Analytical Chemistry, vol. 47, No. 9, Aug. 1975, pp. 1528–1531.

Hess and Marcus, "Analytical Applications of Glow Discharge Devices", Spectroscopy, vol. 2.

Coburn, "Summary Abstract: Diagnostics in plasma processing", Journal of Vacuum Science Technology, vol. 4 (3), May/Jun. 1986, pp. 1830–1832.

Coburn and Kay, "The formation of complexes of the type $X++.R$ in rf rare gas glow discharges", The Journal of Chemical Physics, vol. 6, No. 2, Jan. 1976, pp. 907–908.

Eckstein, Coburn and Kay, "Diagnostics of an R.F. Sputtering Glow Discharge-Correlation Between Atomic Absorption and Mass Spectrometry", International Journal of Mass Spectrometry and Ion Physics, vol. 17, 1975, pp. 129–138.

*Primary Examiner*—Jack I. Berman
*Assistant Examiner*—Kiet T. Nguyen
*Attorney, Agent, or Firm*—Dority & Manning

[57] ABSTRACT

A method and apparatus for analyzing solid sample materials is provided wherein a low pressure glow discharge is initiated by applying a radio frequency potential to an integral, continuous sample cathode and an electrically grounded anode in the presence of an inert gas, the glow discharge being maintained such that the inert gas is ionized and the ionized gas sputters sample material, the sputtered sample material then passing into an analyzer region for analysis.

26 Claims, 15 Drawing Sheets

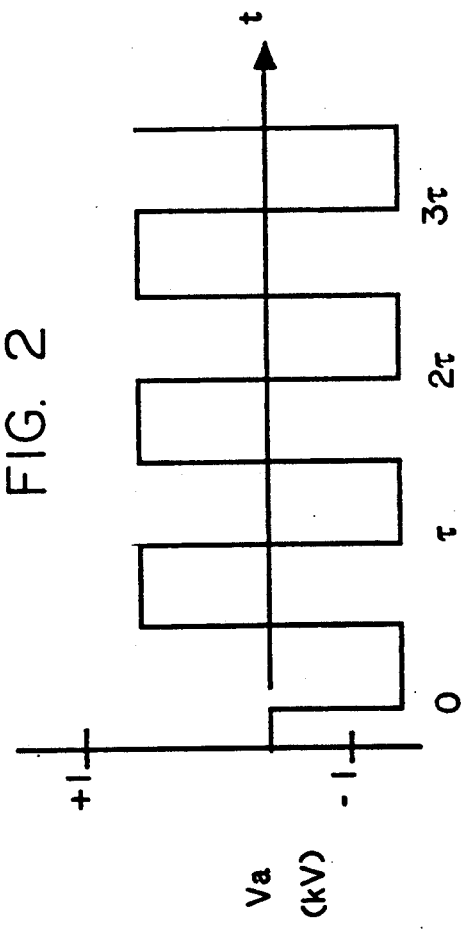
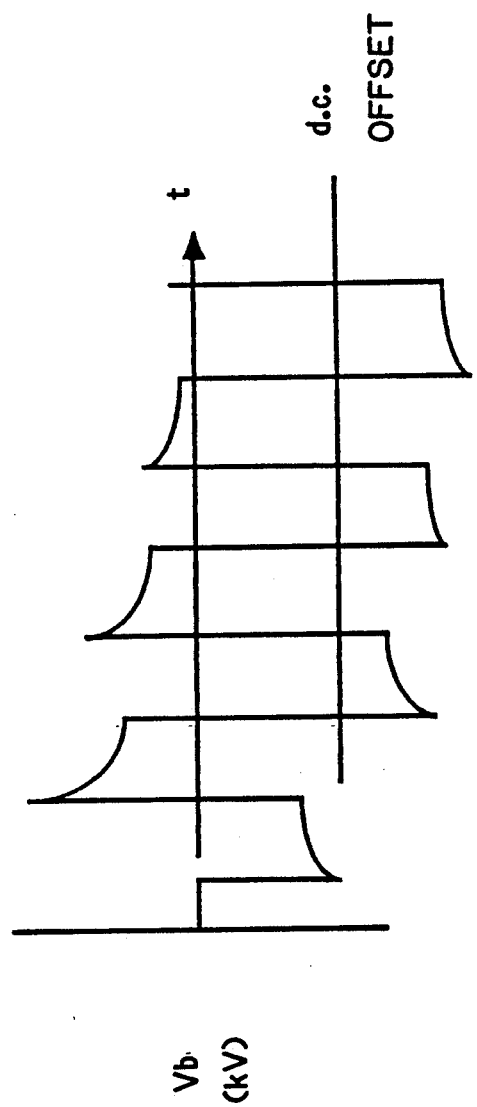
FIG. 2

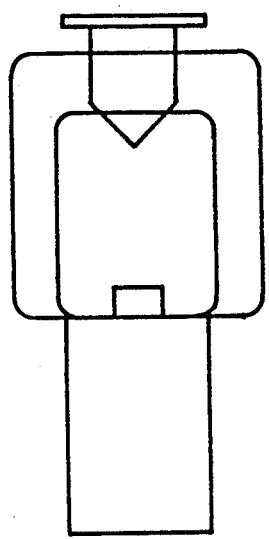
FIG. 10A 25 WATTS, 0.35 torr
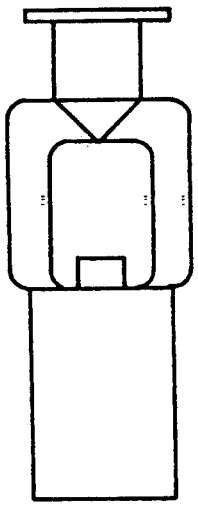
FIG. 10B 25 WATTS, 0.2 torr
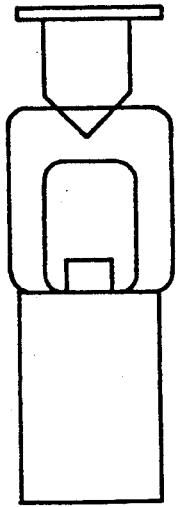
FIG. 10C 25 WATTS, 0.1 torr

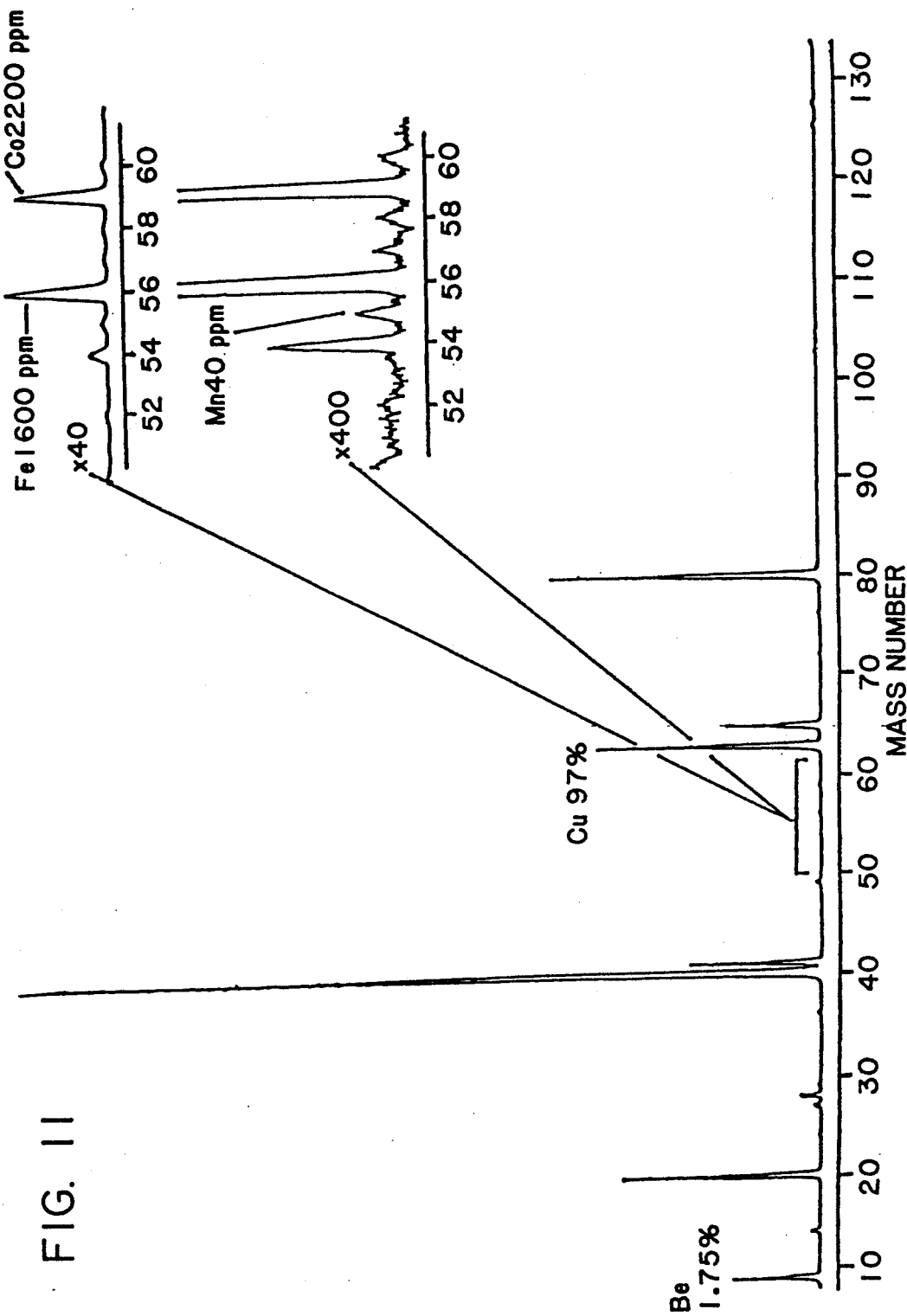

ANALYTICAL METHOD AND APPARATUS

BACKGROUND OF THE INVENTION

The present invention is directed generally to the direct analysis of solids and particularly to a radio frequency powered glow discharge sputtering source for non-conducting solids analysis as well as metals, alloys, semiconductors and the like.

The application of conventional d.c. powered glow discharge devices for the direct analysis of conductive solids such as metals, alloys and semiconductors is well known in the art. Generally, these glow discharge devices are low pressure, inert atmosphere plasmas which rely on cathodic sputtering to atomize solid samples into a "negative glow" region where subsequent excitation and ionization can occur. Most commonly, the conducting sample being analyzed takes the form of a cathode. In a diode design, the sample cathode and an anode sleeve are housed in a vacuum chamber which usually also acts as an anode and is filled with an inert gas such as argon such that a sufficiently high potential placed across the electrodes causes the gas to break down producing electrons and positively charged ions. The negative field potential attracts the discharge ions which hit the cathode surface ejecting atoms, ions and molecules of the cathode material.

By virtue of the electrical biasing, negatively charged species will be accelerated away from and positively charged species returned to the cathode surface. The vast majority of sputtered particles are not charged and can either diffuse back to the cathode surface or into the negative glow. The percentage of atoms entering the discharge excitation region is a function of the discharge pressure and cathode geometry.

The sputtering process acts as a cascade of elastic collisions with the incoming ion imparting some portion of its kinetic energy, which approaches that of the applied potential, into the cathode material's lattice structure. Provided the sputtering ion has sufficient energy and directionality, the cascade will propagate back to the surface resulting in the ejection of cathode material. Sputter yields, the ratio of the average number of sputtered atoms to incident ions, are a function of the relative masses of the collision partners, the incident angle and energy of the sputtering ion, and the cathode material's binding energy.

Glow discharges are currently employed for elemental analysis by atomic absorption, emission, mass spectrometry and a number of laser-based spectroscopic methods. However, these glow discharge sources have been limited by the requirement that the sample be conductive in nature so that it may act as a cathode in a conventional d.c. diode design. In an effort to analyze nonconducting solids without dissolution, nonconducting powder samples have been mixed with a conducting powder matrix. The resulting powder is pressed into a disc sample, which, because of the conductive portion, allows for the required flow of current, but which also permits the sputtering of atoms of the nonconductive material upon impingement by a discharged ion.

This invention, however, is directed to the analysis of nonconducting materials without matrix modification. The use of a radio frequency discharge in argon to sputter and ionize a solid hollow cathode sample for analysis has been described (*Analytical Chemistry*, 47 (9), 1528, 1975). However, the hollow cathode geometry requires that the sample itself be machined into a cylinder which, in addition to the considerable labor involved therein, prevents depth profiling analysis.

The present invention solves the problem of placing a nonconducting analyte in solution by omitting this step and analyzing the solid material directly. Additionally, it solves the problem of machining the nonconducting solid into a cylinder for a hollow cathode electrode configuration by allowing for the direct analysis of discs of the nonconducting material. This capability, especially in combination with the direct insertion probe described herein, provides a much simpler, cheaper and easier to operate system than any prior known means for insulator analysis.

SUMMARY OF THE INVENTION

It is, thus, an object of the present invention to provide a novel method for direct analysis of solids.

It is a further object of the present invention to provide a novel apparatus employing glow discharges to atomize solid samples for direct analysis.

It is yet another object of the present invention to provide an apparatus which employs radio frequency potentials for initiating and maintaining glow discharges.

It is still another object of the present invention to provide a radio frequency powered apparatus for the direct analysis of flat cathode samples and pins.

It is another object of the present invention to provide a method and apparatus for the direct analysis of insulating materials without matrix modification.

It is still a further object of the present invention to provide a method for atomizing solid samples for analysis by spectroscopic techniques including atomic fluorescence, atomic emission, atomic absorption and mass spectrometry.

It is yet another object of the present invention to provide an apparatus for sputtering solid samples for elemental analysis by conventional spectroscopic methods including mass spectrometry, atomic absorption, atomic emission and atomic fluorescence.

It is still another object of the present invention to provide such an apparatus which provides for the fast, successive analysis of a plurality of samples.

These as well as other objects are achieved by providing an apparatus and method for analyzing sample materials in the solid state which have a means for initiating a glow discharge by applying a radio frequency potential to a sample cathode and an electrically grounded anode in the presence of an inert gas such that the gas is ionized and sputters the sample material, as well as a means for passing the sputtered sample material into an analyzer region for analysis. Although a conductive sample can be analyzed by this method, it is specifically designed for the analysis of nonconducting solid materials.

Additionally, a direct insertion probe is provided which precludes pressure changes during disassembly and reassembly of the apparatus for each sample analyzed.

Generally, a sample holder is provided with a stainless steel cylindrical body capped at one end by a plate which has electrical and cooling water connections. The opposite end of the body is enclosed by a cathode mounting plate which has a recess into which the cathode sample is press fit. The holder body may be encased in a glass ceramic sleeve to reduce sputtering of the holder body. An electrically grounded stainless steel anode sleeve is mounted thereabout less than one dark space distance from the holder body. A dark space is the minimum distance required for the formation of a plasma. Thus, the positioning of an anode less than one dark space from the holder body prohibits the formation of a plasma in the enclosed regions. In one embodiment, the entire sample holder/sleeve assembly is mounted on a flange which mates with a six-way cross vacuum apparatus. In the direct insertion probe design, the sample holder/sleeve assembly is easily inserted into and removed from the six-way cross by means of a translator stage.

BRIEF DESCRIPTION OF THE DRAWINGS

FIG. 2 is a graphical representation of the effect of the application of a 2 kV peak-to-peak square wave potential to a pair of electrodes;

FIGS. 10a, 10b and 10c are diagrams illustrating the effect of discharge pressure on dark space thickness;

FIG. 11 is a radio frequency glow discharge mass spectrometry spectrum of a copper-beryllium alloy generated in accordance with the present invention;

DESCRIPTION OF THE PREFERRED EMBODIMENT

The application of d.c. powered glow discharge devices for direct solids analysis is well known. Glow discharge devices are low pressure plasmas that rely on cathodic sputtering to atomize solid samples into a collision-rich negative glow. In the negative glow, sputtered material collides with electrons and metastable discharge gas atoms to produce excited state and ionic species. Conventional d.c. powered glow discharges are currently employed for elemental analysis by atomic absorption, emission, mass spectrometry and a number of laser-based spectroscopic methods.

One of the factors which has tended to limit the application of glow discharges has been the requirement that the sample be conductive in nature. As noted above, nonconducting powder samples have been efficiently atomized for subsequent analysis by mixing with a conducting powder matrix. However, many nonconducting solids are not easily transformed into powders and the transformation of the solid into a powder precludes any depth resolved analyses.

Figure 1:
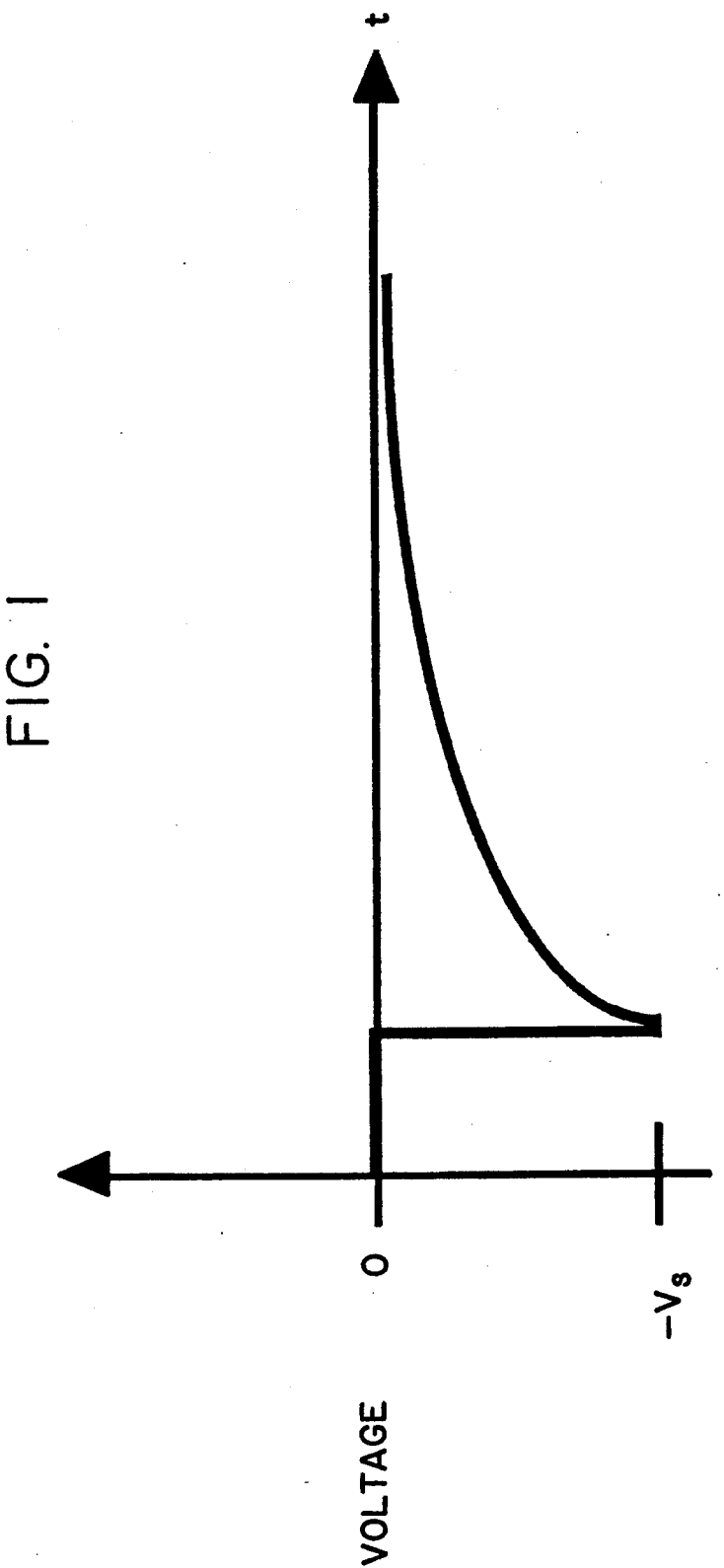
FIG. 1 is a graphical representation of the effect of the application of a high voltage pulse to an insulating surface.

Conventional d.c. glow discharges cannot be used for the sputtering of nonconductive material because, in a d.c. system, if one of the electrodes in the system is an electrically insulating material, the required flow of current cannot occur. The application of a high voltage pulse to an insulating surface can be considered analogous to the charging of a capacitor as shown in FIG. 1. As a high negative voltage ($-V_s$) is applied, the electrode surface potential drops to $-V_s$ followed by a charging to more positive potentials as a function of time. This is not due to the accumulation of positive charges at the surface but rather the loss of electrons through ion neutralization reactions at the surface. The time scale of this process is such that the application of voltage pulses at frequencies on the order of one MHz and above results in a pseudocontinuous plasma.

A key aspect of the application of rf glow discharges to the sputtering of surfaces is the self-biasing which occurs between the plasma electrodes. For example, the application of a 2 kV peak-to-peak square wave potential ($V_a$) to a pair of electrodes is illustrated in FIG. 2. In the initial half-cycle, the voltage of the primary cathode ($V_b$) goes to $-1$ kV and then begins positive charging to approximately $-0.7$ kV. As the applied voltage is switched to $+1$ kV, a half-cycle, electrons are accelerated to the electrode's surface. The greater mobility of the plasma electrons (compared to the much heavier positive ions) results in a faster surface charging during this half-cycle such that the electrode's surface potential approaches zero much faster than the previous half-cycle thus reaching a value of $+0.2$ kV. When the voltage polarity is switched to the start of the second full cycle, the potential on this electrode will reach $-1.8$ kV ($+0.2-2$ kV). As successive cycles proceed, the wave form of $V_b$ will reach a constant offset value which is significantly displaced in the negative direction. This negative d.c. offset (self-biasing), generally having a value of one-half of the applied peak-to-peak potential, is for all intents and purposes continuous. The electrode is bombarded alternately by high energy ions and low energy electrons and is, therefore, employed as the sputtering target (cathode). While the potential supplied to the electrodes are alternating, a time averaged cathode and anode are established. As will be discussed in greater detail below, self-biasing is also a function of the respective electrode sizes. Thus, it is preferable to apply the rf potential to the sputtering target and to make its exposed area much smaller than the vacuum chamber anode which is usually held at ground potential.

Figure 3:
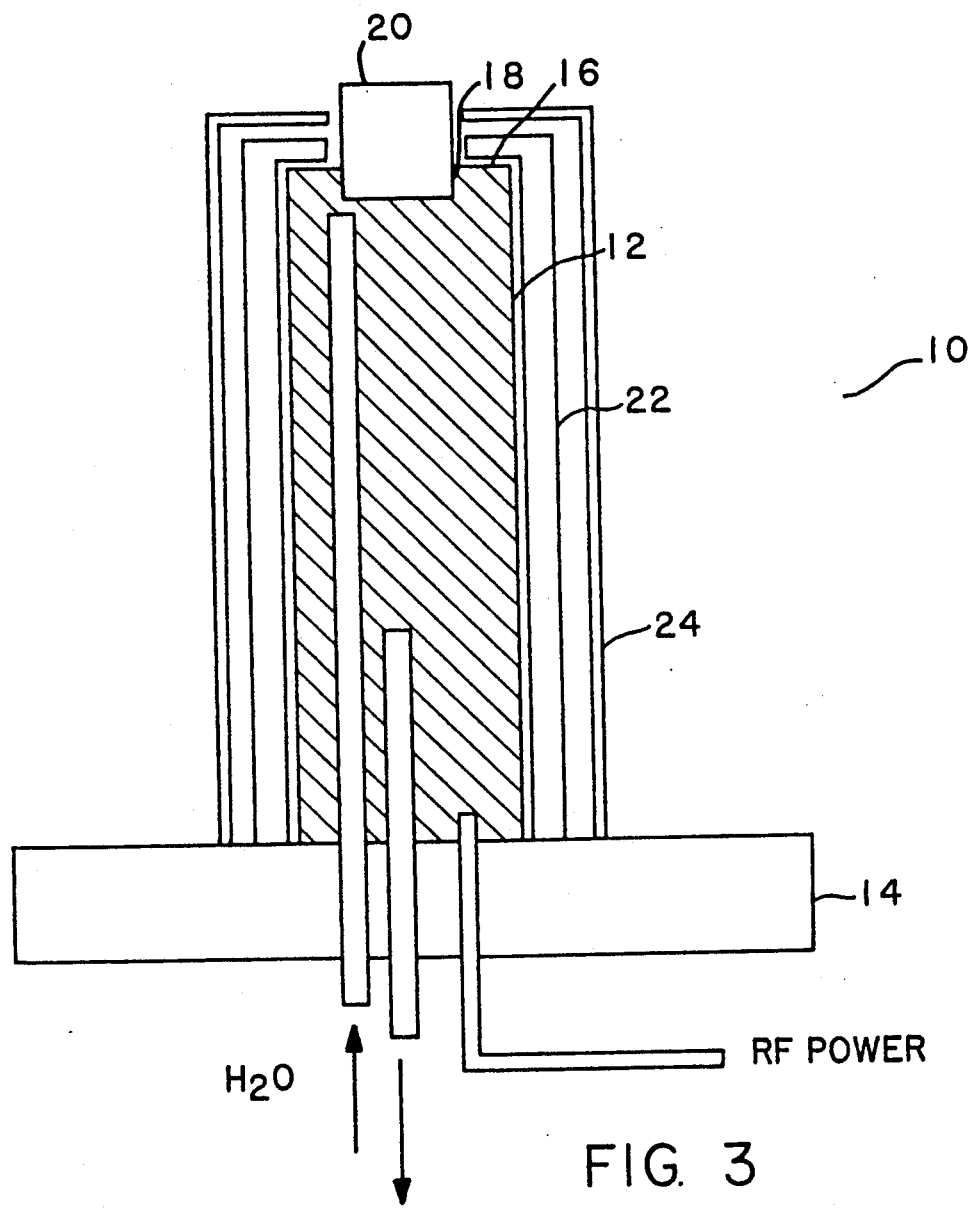
FIG. 3 is a schematic diagram of a sample holder in accordance with the present invention.

Turning now to the design of the apparatus of the present invention, FIG. 3 diagrammatically illustrates a preferred sample holder 10. The body of the holder 12 is a stainless steel cylinder capped at one end by a plate 14 which has electrical and cooling water connections, shown schematically. The opposite end of the body is enclosed by a cathode mounting plate 16 which has a recession 18 preferably 0.5 inches in diameter and 0.125 inches deep into which the sample 20 is press fit. Preferably the holder body is encased in a glass ceramic sleeve 22 which acts to reduce the amount of sputtering of the holder body. An electrically grounded stainless steel "anode" sleeve is mounted thereabout.

The minimum distance required for the formation of a plasma is referred to as a dark space. Thus, the stainless steel sleeve 24 is preferably less than one dark space from the holder body to prohibit the formation of a plasma in the enclosed regions. The entire sample holder/sleeve assembly is mounted on a flange which mates with a six-way cross ion source region described below. Preferably, the inner walls of the vacuum chamber act as an anode.

Figure 4:
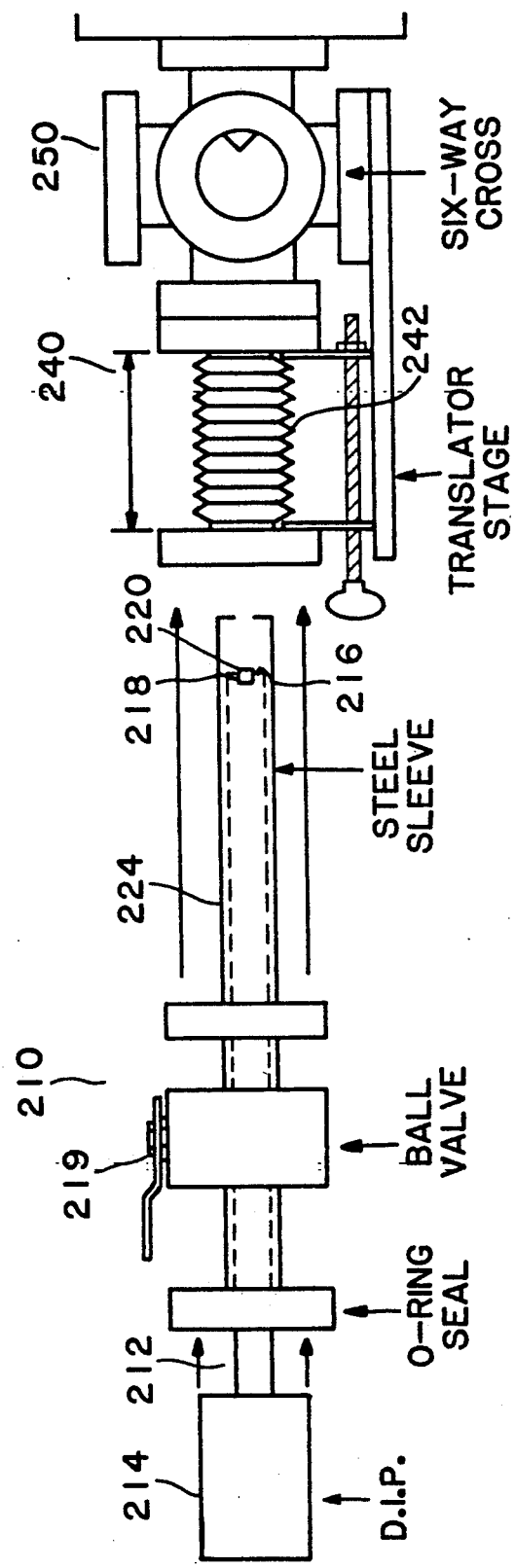
FIG. 4 is an exploded schematic diagram of a direct insertion probe in accordance with the present invention in axial alignment with a translator and a six-way cross.

Alternatively, FIG. 4 schematically illustrates a direct insertion probe for use with the present invention. The probe 210 mates with a six-way cross 250 through a translator stage 240. The translator stage including bellows 242 in conjunction with ball valve 219 serves as a vacuum interlock allowing for insertion and withdrawal of the probe without adjustment of the argon pressure within the six-way cross vacuum chamber providing for faster analysis of a series of samples. A sample holder body 212 is mounted onto the probe 214. A small sample pin 220 is mounted to the sample holder at its tip 216 within a recess 218. A grounded anode cap 224 is drawn over the sample holder and secured thereon. As in the above discussed configurations, the anode cap is within one dark space from the cathode to preclude discharge therein. Thus, a series of sample holders may be provided such that numerous samples can be prepared for a fast, easy analysis of a batch of materials.

In the studies described here, the glow discharge plasma was powered by an RF Plasma Product's Model RF-10 radio frequency generator. This unit has a maximum power output of 1 kW at a frequency of 13.56 MHz. In order to achieve efficient energy transfer to the plasma, an impedance matching network is incorporated in series with the generator. The matching network is an LC circuit which is tuned such that the total impedance of the network and the plasma equal the output impedance of the generator.

Figure 5:
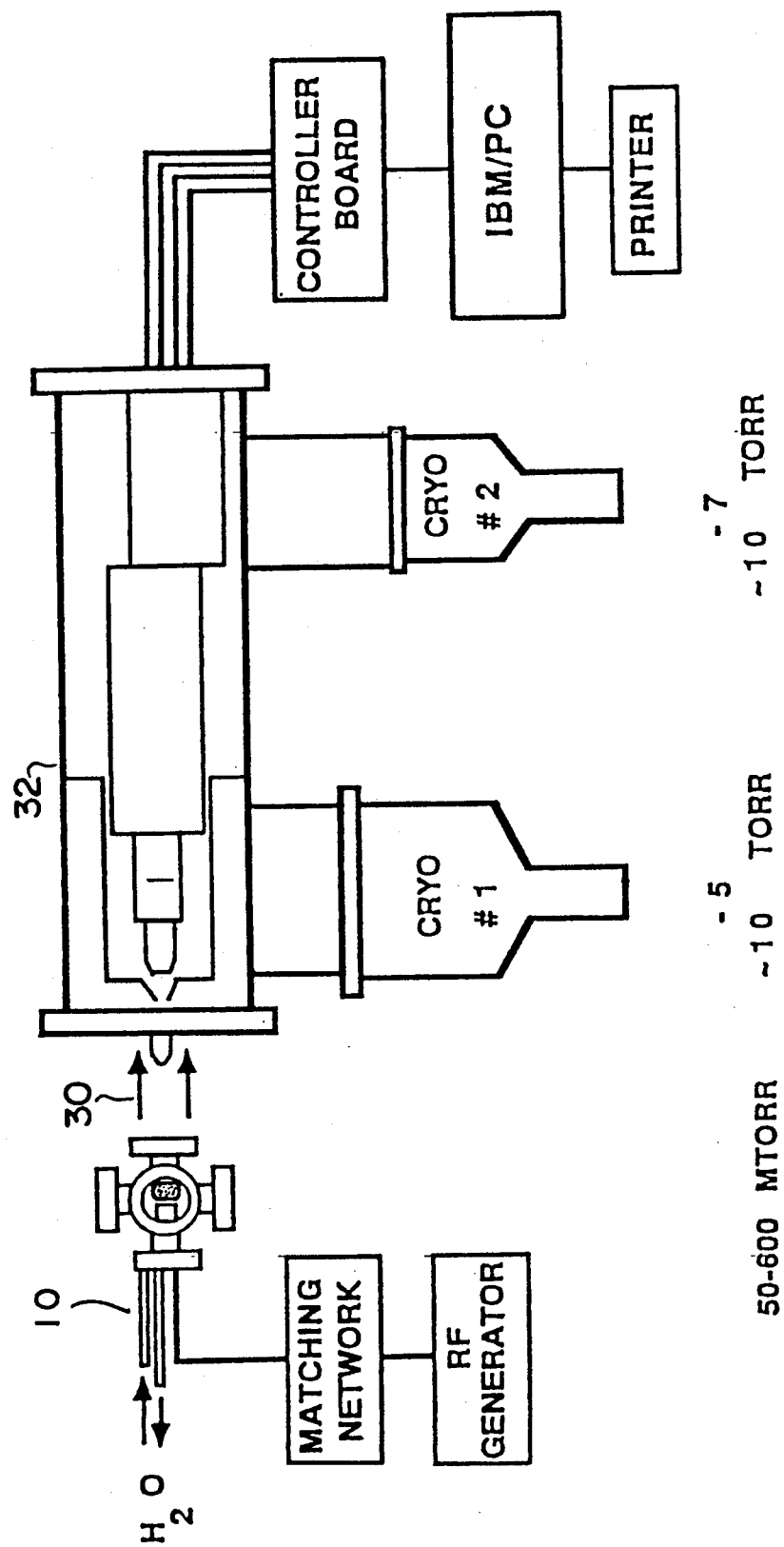
FIG. 5 is a diagram of the present invention as assembled for mass spectrometry analysis.

FIG. 5 is a diagrammatic representation of the apparatus of the present invention as assembled for mass spectrometry analysis. The glow discharge ion source 10 is mounted coaxial with the mass spectrometer axis. The remaining ports of the six-way cross are utilized for the mounting of fused silica optical windows, vacuum and gas inlet attachments, and pressure monitoring thermocouples. Ions generated in the source region pass through an intermediate vacuum region 30 and into the analyzer region 32 for analysis.

Figure 6:
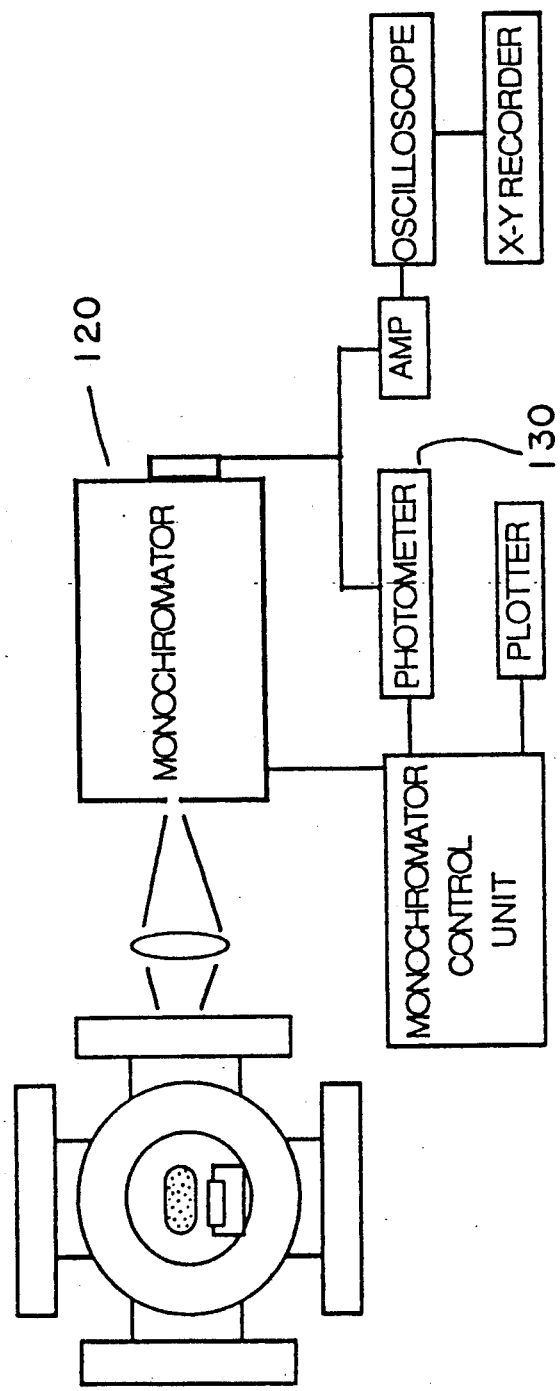
FIG. 6 is a diagram of the present invention as assembled for atomic emission analysis.

Alternatively, FIG. 6 diagrammatically represents the apparatus of the present invention as assembled for atomic emission analysis. The glow discharge ion source is mounted at a 90° angle to the atomic emission axis. Monochromator 120 isolates a narrow region of wavelengths for detection by photometer 130.

Figure 7:
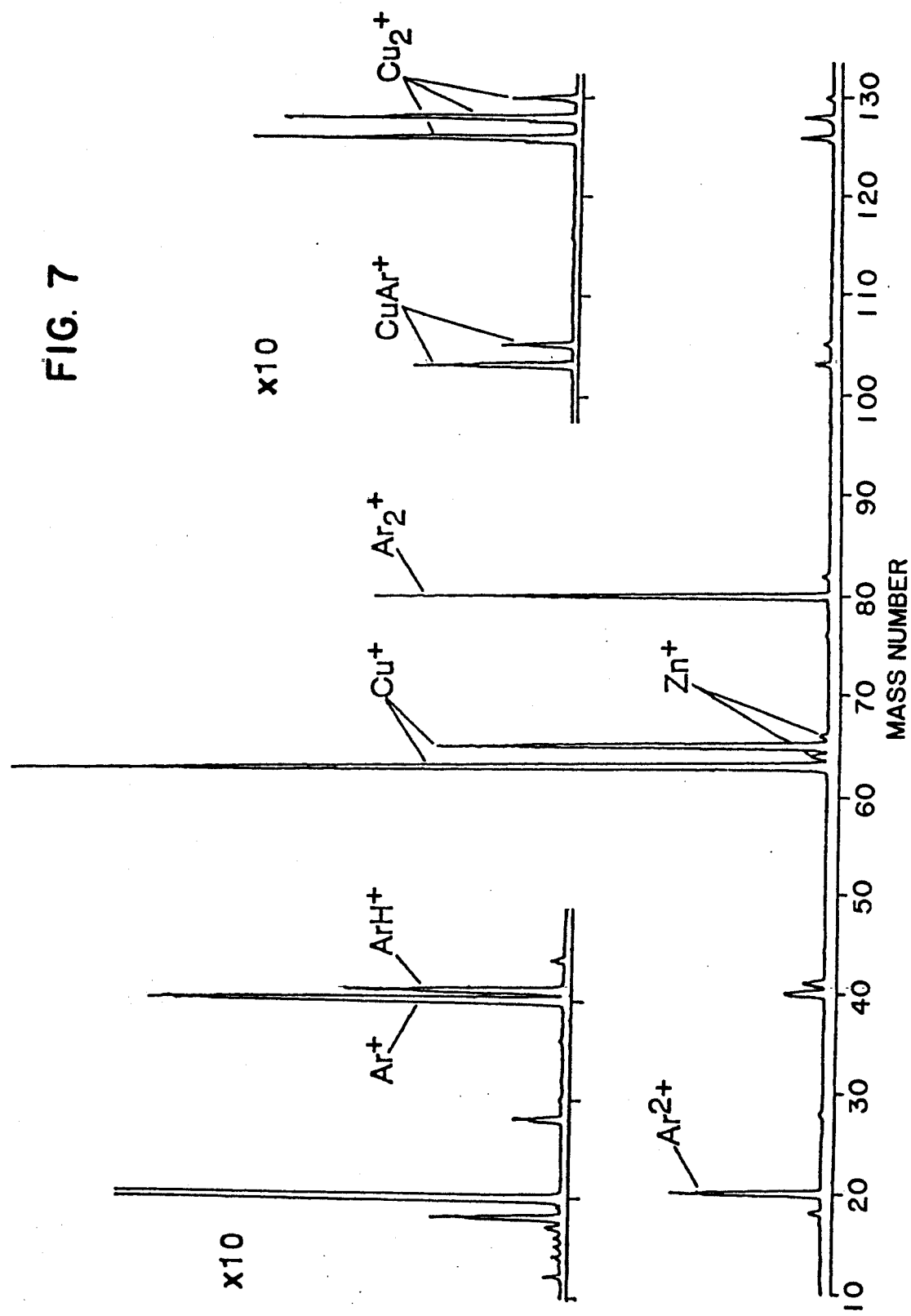
FIG. 7 is a radio frequency glow discharge mass spectrometry spectrum of a copper sample generated in accordance with the present invention.

A preliminary evaluation of the operating parameters of the glow discharge ion source of the present invention was performed employing a conductive sample. A copper metal matrix was chosen because of its ease of sputtering and an earlier d.c. glow discharge mass spectrometric analysis performed on this material. FIG. 7 is the radio frequency-glow discharge mass spectrometry (rf-GDMS) spectrum of the copper sample under discharge conditions of 0.2 torr argon pressure and 10 watts power. The spectra are atomic in nature with the spectrum dominated by ions of the matrix species and various discharge gas species. Scale expansion of the spectrum reveals the existence of species related to residual gases due to non-ideal vacuum conditions: $H_2O^+$ at mass 18, $N_2^+$ at 28, and $CO_2^+$ at mass 44.

Figure 8:
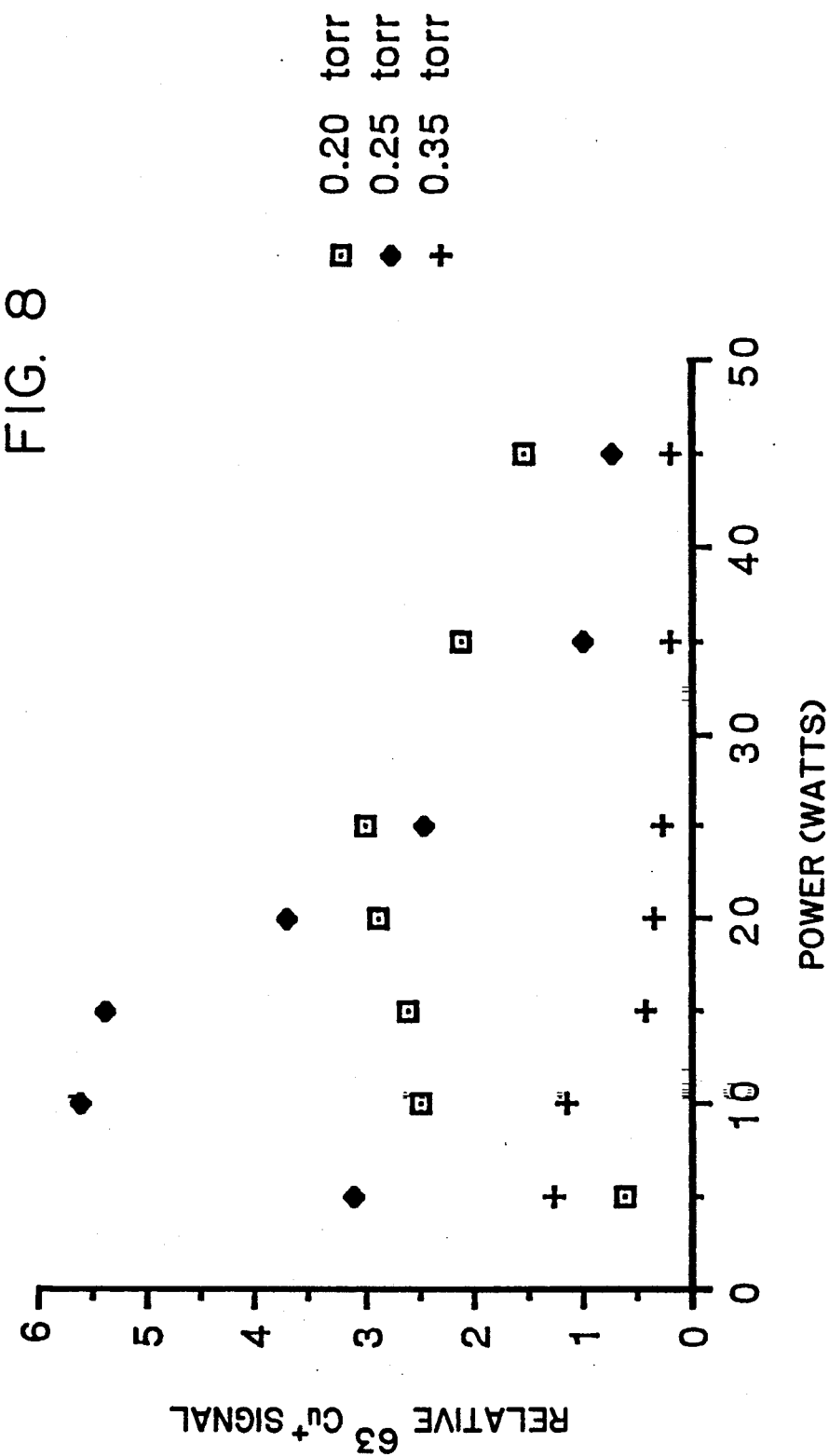
FIG. 8 is a graphical representation of the effect of changes in power and pressure on a copper matrix ion signal generated by the method of the present invention.

The complex interdependency of the pressure-current-voltage conditions of the d.c. plasma sources makes parametric evaluations quite complex; however, the rf source is powered by a constant power generator which makes evaluation somewhat more straightforward. The response of the copper matrix ion signal, specifically, $^{63}CU^+$, to changes of discharge power is shown for a range of pressures in FIG. 8. For each fixed pressure data set, a power is observed where a maximum amount of matrix ion signal is detected. It can be seen that as the discharge pressure increases, the point of the maximum signal shifts to lower power settings. This trend in responses is related to the physical relationship between the plasma negative glow/dark space interface and the ion sampling orifice.

FIGS. 10a, 10b and 10c illustrate the effect of discharge pressure on the dark space thickness and the relationship between the interfacial region and the sampling cone. As discharge pressures decrease, electron mean free paths increase such that the cathode fall (potential drop) occurs over longer distances away from the cathode surface extending the interfacial region toward the exit orifice. Decreases in discharge power (voltage) produce analogous changes though to a much lower degree. Visual observation of the plasma shows a correlation between the position of the negative glow/dark space interface and the matrix ion signal detected. The discharge conditions in which maximum signal is observed are those where the sampling cone orifice is at the interfacial region, the area of greatest ion density, as is shown in FIG. 10b. This spatial relationship is caused by the loss of sufficient energy by secondary electrons emitted from the cathode surface to be effective in direct electron impact ionization collisions with sputtered atoms.

Figure 9:
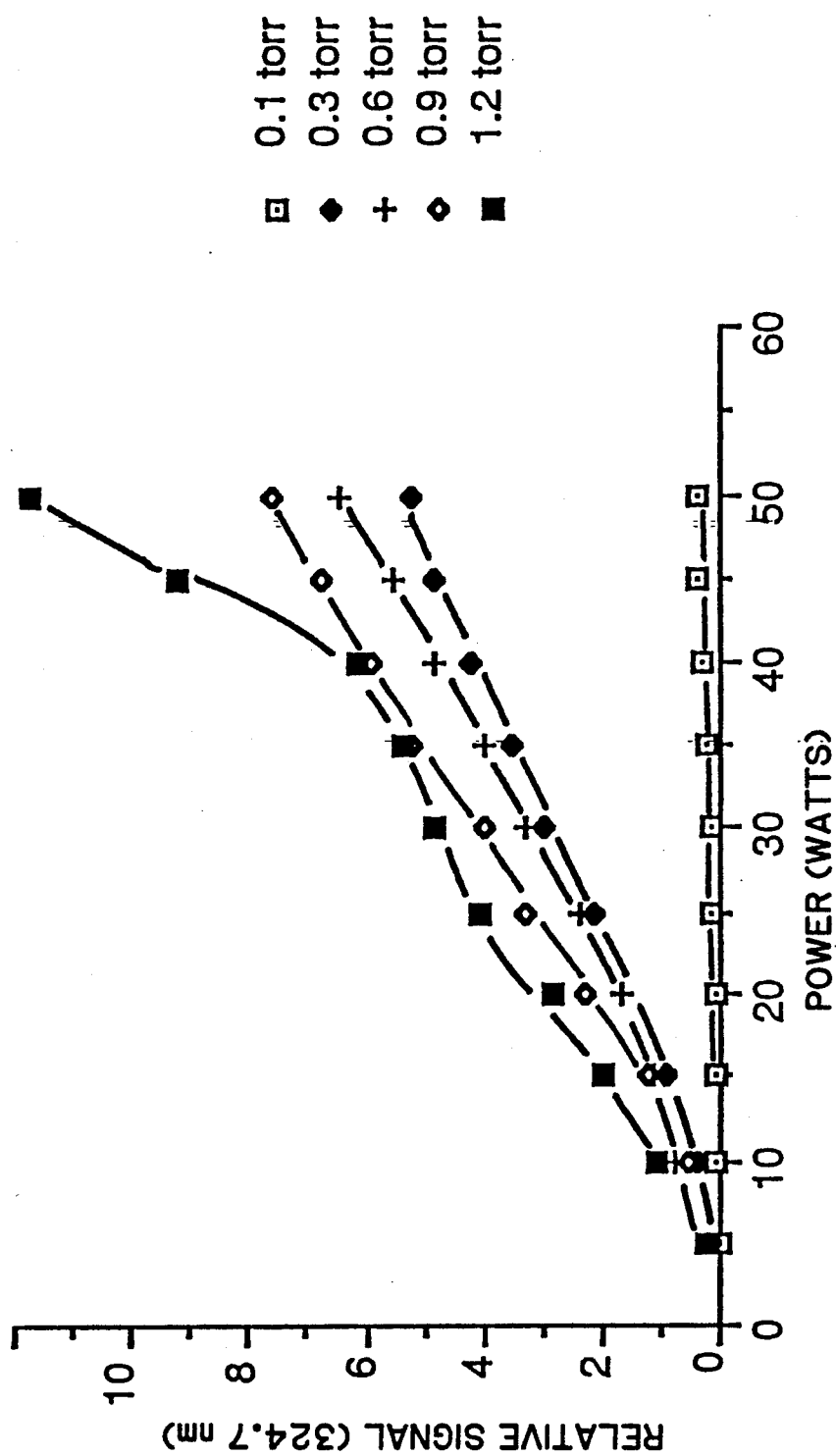
FIG. 9 is a graphical representation of the effect of changes in power and pressure on the copper (I) emission signal generated by the method of the present invention.

Thus, sampling for mass spectrometric analysis is highly regiospecific requiring adjustments of both pressure and power in order to position the negative glow/dark space interface at the sampling cone. In contrast, in an atomic emission analysis, the entire plasma is analyzed resulting in a more straightforward relationship between power and pressure and the relative signal for each species as is illustrated with respect to copper (I) in FIG. 9. Generally, the signal becomes stronger with increased power and increased pressure.

Although for most optical techniques signal strength generally increases with increased pressure, it is often beneficial to maintain relatively low pressures to decrease redeposition. As pressure increases, activity in the plasma increases causing sputtered species to redeposit on the cathode surface. In many applications it is desirable to reduce redeposition as much as possible. For example, in depth profiling the depth of a coating on a sample surface is measured by sputtering the coating, analyzing the sputtered species over time and observing the change in the spectrum to that of the sample material as a function of time. A high level of redeposition caused by a high operating pressure results in sputtered coating species deposited on the exposed sample surface thereby blurring the line between the coating spectra and the sample spectra. Conversely, low operating pressures and correspondingly low redeposition levels provide enhanced depth profiling resolution. Thus, the present rf source provides a fast and inexpensive means for depth profiling with greater resolution capabilities than a conventional d.c. device because of lower operating pressures.

EXAMPLE 1

The application of the glow discharge ion source of the present invention to the analysis of conducting materials is demonstrated in FIG. 11. FIG. 11 is a mass spectrum of the NBS SRM C1122 copper-beryllium alloy under discharge conditions of 0.15 torr argon pressure and 20 watts rf power using the sample holder of FIG. 3. The isotopic signals for the Cu and Be matrix species are clearly seen. The relative sensitivity factors for the iron, cobalt and manganese in the sample are similar to those observed with d.c. glow discharge sources.

Figure 12:
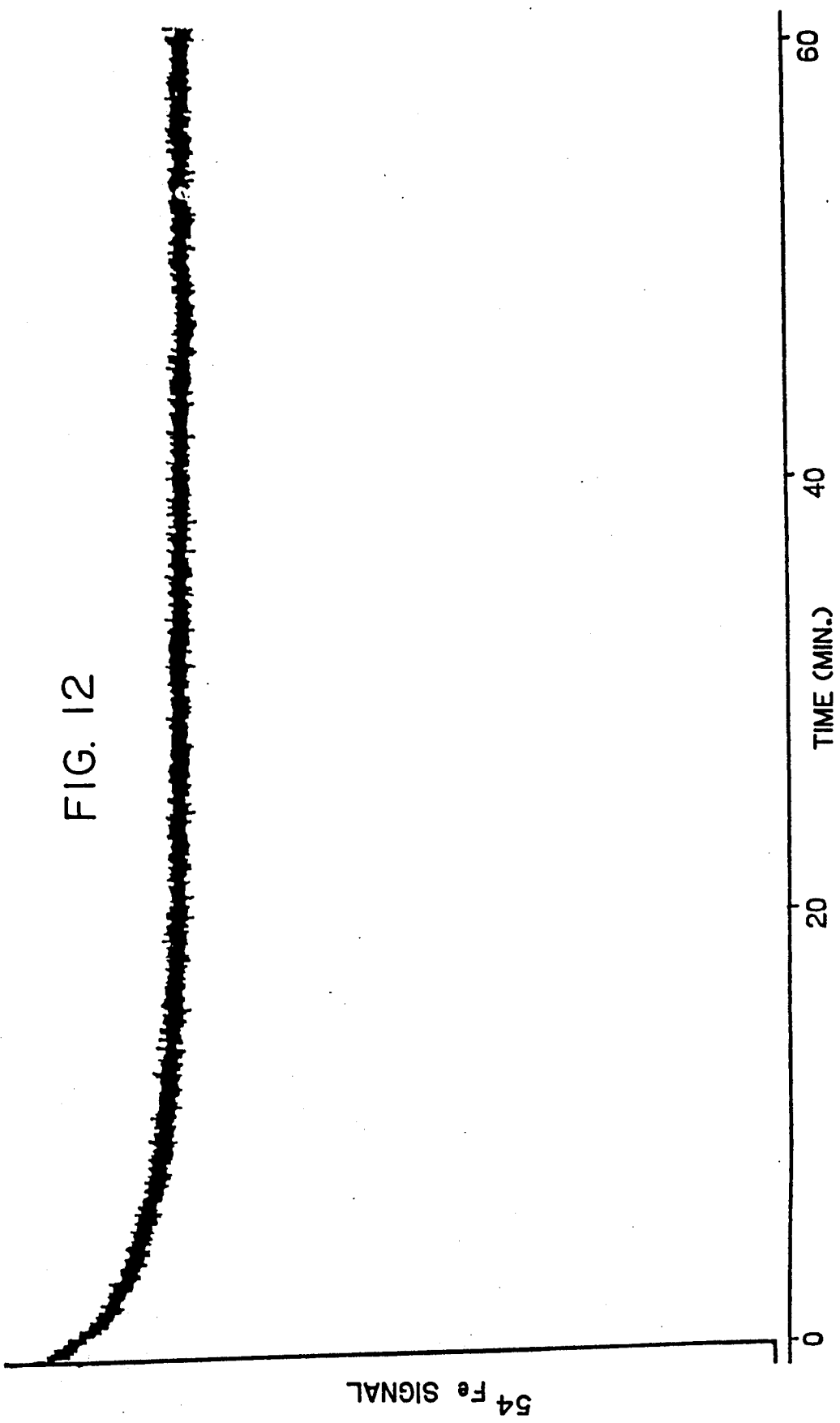
FIG. 12 is a plot of a single ion monitoring trace of a $^{54}$Fe (93 ppm) ion signal as achieved by the present invention.

The ion source operates stably over extended periods of time. FIG. 12 is a single ion monitoring trace of the $^{54}$Fe (93 ppm) ion signal. After an initial 20 minute plasma induction period, the measured ion signal varies by only about 3 percent over the following 40 minute time period. Temporal stability is important for a method such as quadrupole mass spectrometry which is a sequential analysis technique.

EXAMPLE 2

Figure 13:
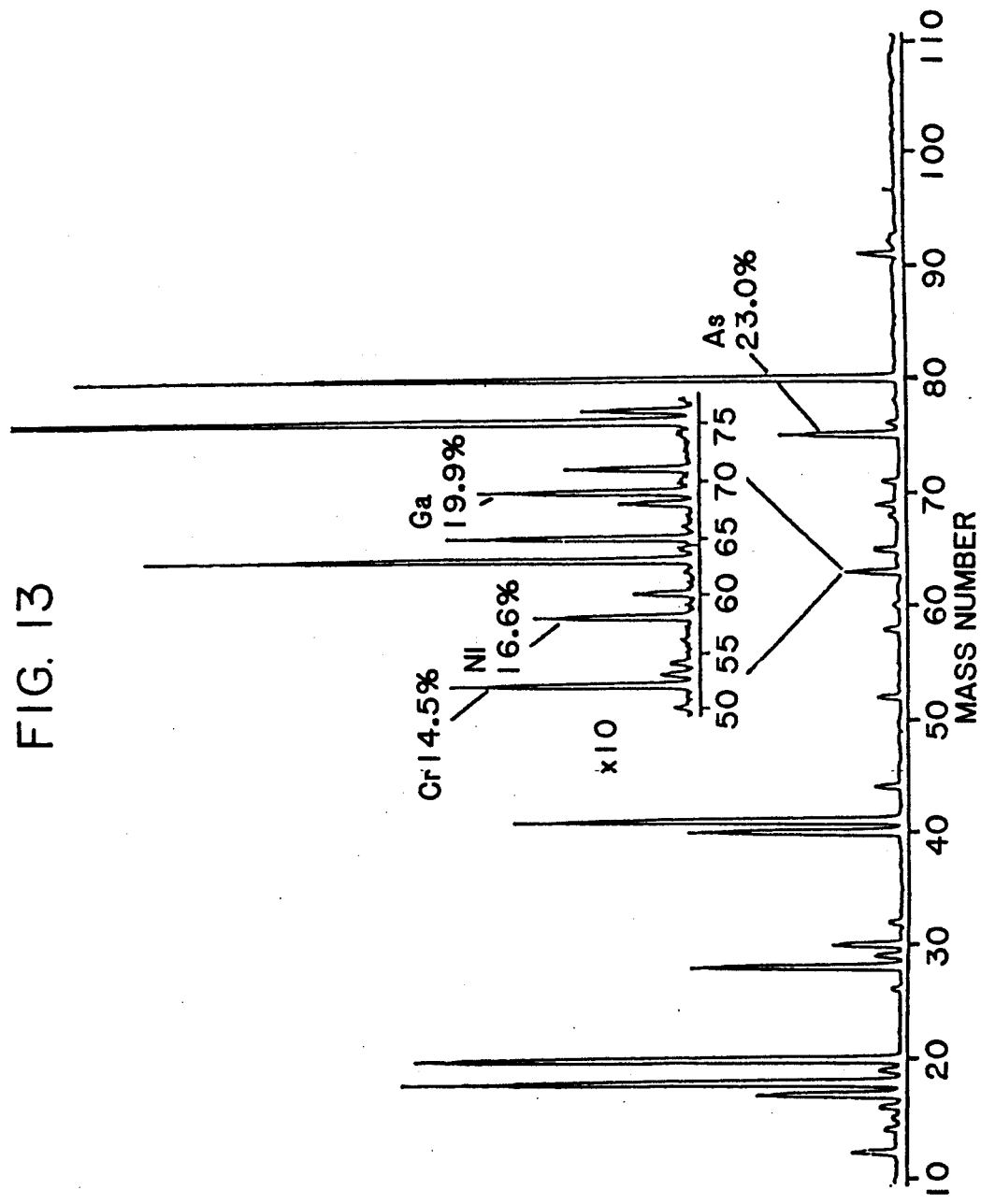
FIG. 13 is a radio frequency glow discharge mass spectrometry spectrum of a pressed disc formed from a mixture of transition metal oxides generated in accordance with the present invention.

To investigate the sputtering of nonconductors, a mixture of transition metal oxides was prepared from Spex (Edison, N.J.) Hi-Pure powders pressed into the form of a disc. Although the sample disc was mounted on a copper backing disc to achieve proper sample positioning with respect to the sampling cone, no conducting powder was added to the mixture and the copper disc was not used to induce current flow as in the prior art d.c. method. The mass spectrum obtained from the mixture which was run under discharge conditions of 0.3 torr argon pressure and 25 watts rf power using the sample holder of FIG. 3 is shown in FIG. 13. As can be clearly seen in the X10 scale expansion, the oxides are efficiently sputtered, dissociated and ionized in elemental form. Although the sample itself is nonconducting, the measured ion current for the metal ions are the same order of magnitude as the metal alloy of Example 1 thus indicating that the oxygen in the sample simply represents an additional element in the matrix which will be sputter atomized like the metal atoms. The spectrum also indicates, through the presence of water and related residual gases, that care should be taken to properly dry and degas the oxide powder samples prior to analysis. The ability to produce atomic ions from a sample of this type is indicative of the applicability of the RF-GDMS source to the analysis of ceramic and cement powders.

EXAMPLE 3

Figure 14:
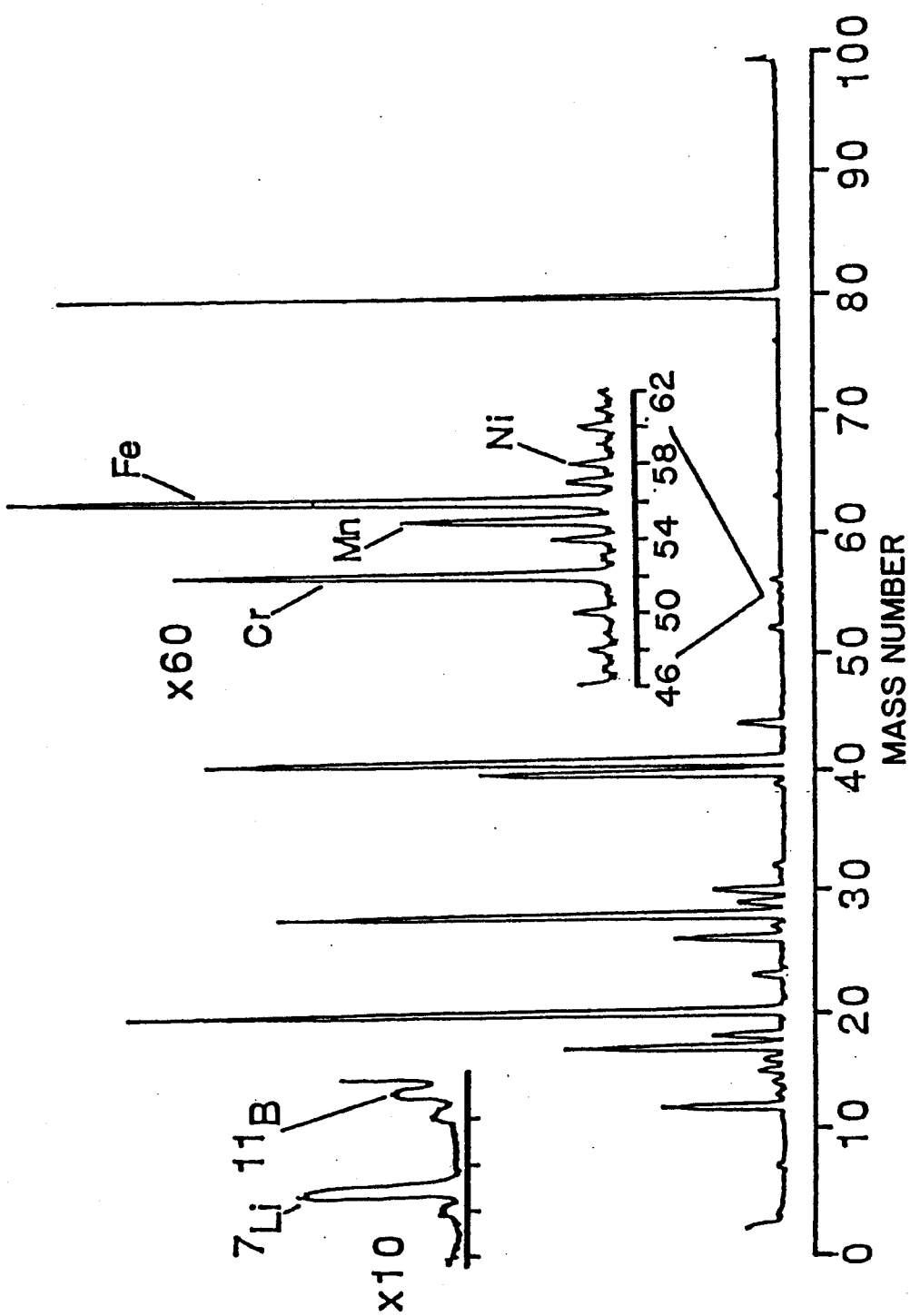
FIG. 14 is a radio frequency glow discharge mass spectrometry spectrum of a vitrified simulated defense waste glass generated in accordance with the present invention.

To investigate the ability of the glow discharge to sputter glass matrix samples, mass spectra were obtained from a glass frit precursor and a vitrified simulated defense waste glass which is commonly employed in the immobilization of high level nuclear waste. As in the case of the metal oxide powders of Example 2, the frit sample was prepared by compacting it into disc form. FIG. 14 is a GDMS spectrum of the vitrified simulated defense waste glass under discharge conditions of 0.15 torr argon pressure and 20 watts rf power using the sample holder of FIG. 3. As was the case for other nonconducting matrices, the plasma was stable.

EXAMPLE 4

Figure 15:
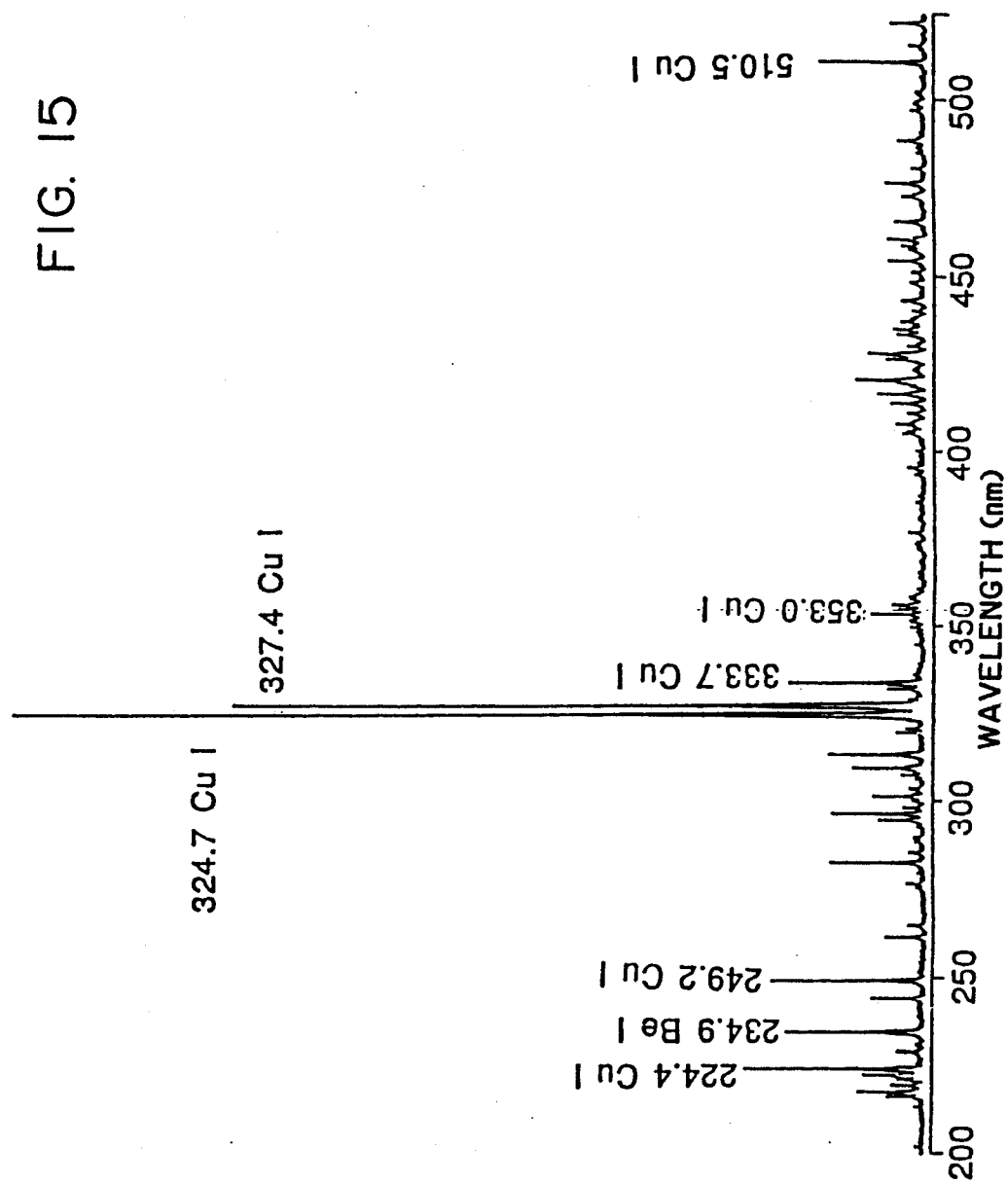
FIG. 15 is a radio frequency glow discharge atomic emission spectrum of a copper-beryllium alloy generated in accordance with the present invention.

The application of the glow discharge ion source of the present invention to the analysis of materials by atomic emission is demonstrated in FIG. 15. FIG. 15 is the emission spectrum of the NBS C1122 copper-beryllium alloy (analyzed by mass spectrometry in Example 1) under discharge conditions of 0.9 torr argon pressure and 15 watts rf power using the sample holder of FIG. 3.

These and other modifications and variations to the present invention may be practiced by those of ordinary skill in the art, without departing from the spirit and scope of the present invention, which is more particularly set forth in the appended claims. Furthermore, those of ordinary skill in the art will appreciate that the foregoing description is by way of example only, and is not intended to be limitative of the invention so further described in such appended claims.

That which is claimed is:

1. A method for analyzing sample materials in the solid state, comprising:
    initiating a low pressure glow discharge by applying a radio frequency potential between a solid sample cathode and an anode in the presence of an inert gas;
    maintaining the glow discharge such that the inert gas is ionized and the ionized gas sputters substantially only sample material;
    passing the sputtered sample material into an analyzer region; and
    analyzing the sputtered sample material.

2. The method set forth in claim 1 wherein the glow discharge is maintained at a low pressure to reduce redeposition of the sputtered sample material onto the sample cathode.

3. A source for mass spectrometric analysis of solid samples comprising:
    a six-way cross vacuum chamber;
    a mass spectrometer associated with a port of said six-way cross;
    means for introducing an inert gas into said six-way cross;
    a sample holder adapted to a port of said six-way cross comprising:
        a holder body having electrical connections thereon;
        a mounting plate at one end of the holder body defining a recess therein for receiving a sample cathode; and
        an anode sleeve mounted about the holder body at a distance from the holder body less than the distance required to form a plasma thereby precluding the formation of a plasma within the anode sleeve;
    means for applying a radio frequency potential to initiate a plasma adjacent the sample cathode; and
    a sampling cone associated with the mass spectrometer positionable adjacent the sample at said distance required to form a plasma.

4. A method for analyzing sample material in the solid state, comprising:

providing a solid sample cathode and an anode in the presence of an inert gas;

initiating a low pressure glow discharge by applying a radio frequency potential between said sample cathode and said anode where said anode is at a distance greater than one dark space distance from said cathode;

precluding the formation of a glow discharge in desired areas by positioning an anode within one dark space distance from said cathode at said areas;

maintaining the glow discharge such that inert gas is ionized and the ionized gas sputters sample material;

passing the sputtered sample material into an analyzer region; and analyzing the sputtered material.

5. A method of analyzing a nonconductive material comprising the steps of:

locating an unadulterated sample of said nonconductive material in a holder therefor to form a cathode;

placing said holder and said sample in a low pressure chamber;

initiating glow discharge within said chamber by applying a radio frequency potential between an anode and said cathode in the presence of an inert gas;

maintaining said glow discharge in said chamber such that said inert gas is ionized and the ionized as sputters said sample while at least substantially shielding said holder against sputtering;

passing the sputtered sample material into an analyzer region; and analyzing said sputtered sample material.

6. A sample holder for solid nonconductive sample materials for elemental analysis comprising:

a conductive sample holder body, said body being adapted for connection to a source of radio frequency energy, said holder further defining a recess in an end of same for receipt of a sample of a material to be analyzed, said sample holder further having an anode located around said holder and defining an opening about said sample, said anode being spaced from said holder at a distance therefrom inadequate for the formation of a plasma therebetween, so that when said holder with a sample received thereon is inserted into a chamber for analysis of the sample and a radio frequency potential is produced between the sample holder and an anode located apart from the sample holder adequate for the formation of plasma in the pressure of an inert gas, substantially only the sample will be sputtered.

7. An apparatus for the direct analysis of integral, continuous solid samples without matrix modification comprising:

a six-way cross vacuum chamber;

means for analytical analysis associated with a port of said six-way cross;

pumping means associated with a port of said six-way cross for introducing an inert gas at specified pressures;

a sample holder adapted to a port of said six-way cross, comprising:

a holder body having electrical connections thereon;

a mounting plate at one end of the holder body defining a recess therein for receiving a sample cathode; and an anode sleeve mounted about the holder body for precluding the formation of a plasma within the sleeve about the holder body; and means for introducing a radio frequency potential to initiate and maintain a plasma adjacent said sample cathode.

8. The apparatus set forth in claim 7 wherein the six-way cross is an anode.

9. The apparatus set forth in claim 7 wherein the inert gas is argon.

10. The apparatus set forth in claim 7 wherein the anode sleeve is electrically grounded.

11. The apparatus set forth in claim 7 further including a ceramic sleeve between the holder body and the anode sleeve to further preclude the formation of a plasma about the holder body.

12. A sample holder for supporting a solid sample for use in generating a plasma comprising:

a holder body, said body being adapted for electrical connection, said body defining a recess at one end of same for receipt of a solid sample cathode; and an anode sleeve mounted about said holder body at a distance from said holder body less than the distance required to form a plasma, said sleeve defining an opening therein adequate to expose said sample to a plasma to be generated for sputtering.

13. The sample holder set forth in claim 12 wherein said holder body further includes cooling water connections.

14. The sample holder set forth in claim 12 wherein said holder body is a stainless steel cylinder.

15. The sample holder set forth in claim 12 wherein said mounting plate is integral with said holder body.

16. The sample holder set forth in claim 12 wherein said anode sleeve is stainless steel.

17. The sample holder set forth in claim 12 wherein said anode sleeve is electrically grounded.

18. A sample holder as defined in claim 12 wherein a ceramic sleeve is mounted between said body and said anode sleeve.

19. Apparatus for direct analysis of solid unadulterated samples comprising:

(a) a multiport chamber;

(b) an analytical analysis unit associated with one port of said multiport chamber for receiving sample material therethrough for analysis;

(c) means associated with one port of said multiport chamber for introducing an inert gas thereinto at predetermined pressures;

(d) locking means associated with one port of said chamber for receipt of a sample carrying probe therethrough and for closing said chamber when a probe is not associated therewith; and (e) a probe adapted to be received through said locking means for introduction of a sample to be analyzed into said chamber, said probe comprising:

a probe body;

a sample holder carried by said probe body and defining a recess therein for receipt of a sample to analyzed, an anode cover receivable about said body holder at a distance from said holder less than the distance required to form a plasma therebetween;

valve means carried on said probe matable with said locking means when said probe is inserted therethrough to define a seal thereat so that said probe may be inserted into said chamber and removed therefrom while said chamber is maintained at a constant predetermined pressure; and means for introducing a radio frequency potential within said chamber between an anode therein and said probe to initiate and maintain a plasma adjacent said sample cathode, with no plasma being produced between said anode sleeve of said probe and said sample holder.

20. The apparatus set forth in claim 19 wherein the multiport chamber is an anode.

21. The apparatus set forth in claim 19 wherein the inert gas is argon.

22. The apparatus set forth in claim 19 wherein the anode cap is electrically grounded.

23. The apparatus set forth in claim 19 wherein the means for analytical analysis is mass spectrometry.

24. The apparatus set forth in claim 19 wherein the means for analytical analysis is atomic emission.

25. The apparatus set forth in claim 19 wherein the means for analytical analysis is atomic absorption.

26. A method as defined in claim 19 wherein said anode located within one dark space from said cathode at certain areas where glow discharge is to be precluded is a separate anode.

* * * * *